US011135574B2

(12) United States Patent
Jantharasuk et al.

(10) Patent No.: US 11,135,574 B2
(45) Date of Patent: Oct. 5, 2021

(54) CATALYST SYSTEM AND PROCESS FOR CONVERSION OF A HYDROCARBON FEED UTILIZING THE CATALYST SYSTEM

(71) Applicant: SMH Co., Ltd, Bangkok (TH)

(72) Inventors: Amnart Jantharasuk, Rayong (TH); Kongkiat Suriye, Samut-Prakan (TH)

(73) Assignee: SMH Co., Ltd, Bangkok (TH)

( * ) Notice: Subject to any disclaimer, the term of this patent is extended or adjusted under 35 U.S.C. 154(b) by 0 days.

(21) Appl. No.: 16/468,746

(22) PCT Filed: Nov. 16, 2017

(86) PCT No.: PCT/EP2017/079489
§ 371 (c)(1),
(2) Date: Jun. 12, 2019

(87) PCT Pub. No.: WO2018/108441
PCT Pub. Date: Jun. 21, 2018

(65) Prior Publication Data
US 2019/0314796 A1    Oct. 17, 2019

(30) Foreign Application Priority Data

Dec. 13, 2016 (EP) ..................... 16203692

(51) Int. Cl.
*B01J 29/16* (2006.01)
*B01J 29/85* (2006.01)
(Continued)

(52) U.S. Cl.
CPC ............... *B01J 29/85* (2013.01); *B01J 23/28* (2013.01); *B01J 23/30* (2013.01); *B01J 23/36* (2013.01); *B01J 23/42* (2013.01); *B01J 23/44* (2013.01); *B01J 23/468* (2013.01); *B01J 29/035* (2013.01); *B01J 29/0354* (2013.01); *B01J 29/0356* (2013.01); *B01J 29/0358* (2013.01); *B01J 29/061* (2013.01); *B01J 29/068* (2013.01); *B01J 29/072* (2013.01); *B01J 29/076* (2013.01); *B01J 29/166* (2013.01); *B01J 29/40* (2013.01); *B01J 29/44* (2013.01); *B01J 29/46* (2013.01); *B01J 29/48* (2013.01); *B01J 29/89* (2013.01); *B01J 35/0006* (2013.01); *B01J 37/0215* (2013.01); *B01J 37/0244* (2013.01); *B01J 37/0246* (2013.01); *B01J 37/0248* (2013.01); *B01J 37/04* (2013.01); *C07C 4/08* (2013.01); *C07C 4/18* (2013.01); *C07C 6/02* (2013.01); *C07C 6/04* (2013.01); *C07C 9/10* (2013.01); *C07C 9/14* (2013.01); *C07C 11/04* (2013.01); *C10G 49/08* (2013.01); *C10G 55/06* (2013.01); *C10G 63/04* (2013.01); *C10G 65/02* (2013.01); *B01J 2229/186* (2013.01); *B01J 2229/20* (2013.01); *B01J 2229/42* (2013.01);
(Continued)

(58) Field of Classification Search
CPC ................ B01J 2229/20; B01J 2229/42; B01J 2229/186; B01J 29/40; B01J 29/85; B01J 29/89; B01J 29/166; B01J 29/061; B01J 29/068; B01J 29/072; B01J 29/076; B01J 29/0358; B01J 29/035; B01J 29/0354; B01J 29/0356; B01J 29/44; B01J 29/46; B01J 29/48; B01J 35/0006; B01J 37/04; B01J 37/0215; B01J 37/0244; B01J 37/0246; B01J 37/0248; B01J 23/28; B01J 23/468; B01J 23/30; B01J 23/005; B01J 23/26; B01J 23/44; B01J 23/42; B01J 23/36; C10G 2400/20; C10G 63/04; C10G 65/02; C10G 65/12; C10G 49/08; C10G 55/06; Y02P 20/52; C07C 2529/40; C07C 2529/70; C07C 2529/85; C07C 2529/035; C07C 2529/89; C07C 2529/16; C07C 2529/068; C07C 2529/072; C07C 2529/076; C07C 2529/44; C07C 2529/46; C07C 2529/48; C07C 2529/74; C07C 2529/76; C07C 2529/78; C07C 2523/63; C07C 2523/22; C07C 2523/26; C07C 2523/28; C07C 2523/30; C07C 2523/42; C07C 2523/44; C07C 2523/46; C07C 4/08; C07C 4/18; C07C 11/04; C07C 6/02; C07C 6/04
USPC ........ 502/60, 63, 64, 65, 66, 67, 68, 69, 73, 502/74, 77, 527.12, 527.13; 585/500, 585/520, 530, 531, 533; 208/46, 62, 66, 208/134, 135, 136, 138, 141
See application file for complete search history.

(56) References Cited

U.S. PATENT DOCUMENTS 3,980,721 A    9/1976 Juguin et al.
2004/0152586 A1*  8/2004  Ou ..................... B01J 23/002
                                                          502/64
(Continued)

FOREIGN PATENT DOCUMENTS

EP    2689843 A1    1/2014
EP    3069788 A1    9/2016

OTHER PUBLICATIONS

Jan. 29, 2018, International Search Report and Written Opinion, PCT/EP2017/079489.

*Primary Examiner* — Elizabeth D Wood
(74) *Attorney, Agent, or Firm* — Banner & Witcoff, Ltd.

(57) ABSTRACT

The present invention relates to a catalyst system comprising: i. a first layer of a hydrocarbon conversion catalyst, the hydrocarbon conversion catalyst comprising: a first composition comprising a platinum group metal on a solid support; and a second composition comprising a transition metal on an inorganic support; ii. a second layer comprising a cracking catalyst; and to a process for conversion of a hydrocarbon feed utilizing this catalyst system.

19 Claims, No Drawings

(51) Int. Cl.

| | |
|---|---|
| B01J 23/28 | (2006.01) |
| B01J 23/30 | (2006.01) |
| B01J 23/36 | (2006.01) |
| B01J 23/42 | (2006.01) |
| B01J 23/44 | (2006.01) |
| B01J 23/46 | (2006.01) |
| B01J 29/40 | (2006.01) |
| B01J 35/00 | (2006.01) |
| B01J 37/04 | (2006.01) |
| C07C 4/18 | (2006.01) |
| C07C 9/10 | (2006.01) |
| C07C 9/14 | (2006.01) |
| B01J 29/072 | (2006.01) |
| B01J 29/89 | (2006.01) |
| B01J 29/076 | (2006.01) |
| B01J 29/035 | (2006.01) |
| B01J 29/44 | (2006.01) |
| B01J 29/068 | (2006.01) |
| B01J 29/06 | (2006.01) |
| B01J 29/48 | (2006.01) |
| B01J 29/46 | (2006.01) |
| B01J 37/02 | (2006.01) |
| C10G 55/06 | (2006.01) |
| C10G 49/08 | (2006.01) |
| C10G 63/04 | (2006.01) |
| C10G 65/02 | (2006.01) |
| C07C 6/04 | (2006.01) |
| C07C 11/04 | (2006.01) |
| C07C 6/02 | (2006.01) |
| C07C 4/08 | (2006.01) |

(52) U.S. Cl.
CPC ...... *C07C 2523/22* (2013.01); *C07C 2523/26* (2013.01); *C07C 2523/28* (2013.01); *C07C 2523/30* (2013.01); *C07C 2523/42* (2013.01); *C07C 2523/44* (2013.01); *C07C 2523/46* (2013.01); *C07C 2523/63* (2013.01); *C07C 2529/035* (2013.01); *C07C 2529/068* (2013.01); *C07C 2529/072* (2013.01); *C07C 2529/076* (2013.01); *C07C 2529/16* (2013.01); *C07C 2529/40* (2013.01); *C07C 2529/70* (2013.01); *C07C 2529/78* (2013.01); *C07C 2529/85* (2013.01); *C07C 2529/89* (2013.01); *C10G 2400/20* (2013.01)

(56) References Cited

U.S. PATENT DOCUMENTS

| | | | |
|---|---|---|---|
| 2007/0106089 A1* | 5/2007 | Benderly | C07C 57/04 560/211 |
| 2010/0274063 A1* | 10/2010 | Wang | C10G 11/05 585/324 |
| 2011/0105784 A1* | 5/2011 | Benderly | C07C 67/39 560/205 |
| 2015/0329438 A1* | 11/2015 | Nyce | C07C 1/12 518/705 |
| 2016/0200643 A1* | 7/2016 | Nyce | F25J 3/0209 585/329 |

* cited by examiner

CATALYST SYSTEM AND PROCESS FOR CONVERSION OF A HYDROCARBON FEED UTILIZING THE CATALYST SYSTEM

CROSS-REFERENCE TO RELATED APPLICATIONS

This application is a U.S. National Stage application under 35 U.S.C. § 371 of International Application PCT/EP2017/079489 (published as WO 2018/108441 A1), filed Nov. 16, 2017, which claims the benefit of priority to Application EP 16203692.5, filed Dec. 13, 2016. Benefit of the filing date of each of these prior applications is hereby claimed. Each of these prior applications is hereby incorporated by reference in its entirety.

The present invention relates to a catalyst system and a process for conversion of a hydrocarbon feed comprising a saturated hydrocarbon compound to olefin products.

Olefins, especially light olefins including ethylene and propylene, are valuable hydrocarbon products. They are useful for preparing a wide variety of end products, including ethylene oxide, propylene oxide, ethyl benzene, acetone, phenol, polyethylene, polypropylene, other polymers, and other petrochemical products. Even though their prices have fluctuated over time, the demands in the industry have still been continuously growing.

To serve industrial needs, many methods have been used to produce olefins. However, it is typically more economically attractive to produce olefins from lower valued feedstock such as paraffins. A conventional method for converting saturated paraffins to olefins is thermal cracking. This is a highly energy intensive method and the product selectivity is difficult to be adjusted and controlled.

Catalytic cracking is a later developed method. With appropriate catalytic materials, generally zeolite-based materials, hydrocarbon cracking can occur at less severe operating conditions.

In the art, also processes are known converting saturated paraffins to olefins by dehydrogenation utilizing an appropriate catalyst. The dehydrogenation may be followed by an appropriate metathesis step, in order to finally provide an olefin distribution which fulfills highest industrial needs.

A drawback of such hydroconversion processes is that it tends to produce high amounts of higher olefin, such as butenes, although lower olefin, such as ethylene, is some times more commercially attractive.

It is therefore an object of the present invention to provide a catalyst system and a process utilizing it for the conversion of hydrocarbons wherein the amount of higher olefins as a product is decreased, hut the amount of lower olefins, especially ethylene, is increased.

This object is achieved by a catalyst system comprising:
i. a first layer of a hydrocarbon conversion catalyst, the hydrocarbon conversion catalyst comprising:
   a first composition comprising a dehydrogenation active metal on a solid support; and
   a second composition comprising a transition metal on an inorganic support; and
ii. a second layer comprising a cracking catalyst.

In the hydrocarbon conversion catalyst, it may be provided that the first composition is different from the second composition. Likewise, the solid support comprised in the first composition may be different from the inorganic support comprised in the second composition. Similarly, the dehydrogenation active metal comprised in the first composition is preferably different from the transition metal comprised in the second composition.

It may be provided that the second composition does not comprise the dehydrogenation active metal, in particular the second composition does not comprise platinum, palladium, rhodium, chromium or mixtures thereof.

In a further embodiment, the inorganic support comprised in the second composition comprises $SiO_2$, HY-zeolite or mixtures thereof and the solid support comprised in the first composition comprises a mixture of silica and zirconia.

In one embodiment, the cracking catalyst is for cracking olefins, preferably for cracking butene into ethylene.

In one embodiment, the cracking catalyst comprises a molecular sieve, preferably zeolite and/or silicalite.

In another embodiment, the cracking catalyst consists of a molecular sieve, preferably zeolite and/or silicalite.

Molecular sieve is a material well-known in the art having very small pores of precise and uniform size which will selectively absorb molecules that can pass through the pores. Some examples include activated charcoal, silica gel, silicalite, and natural or synthetic zeolite.

Zeolites are well-known as natural or synthetic hydrated aluminosilicate compounds with well-defined crystalline structure and cage-like cavities. The structures of zeolites are based on three-dimensional frameworks of silica and alumina tetrahedra.

In one embodiment, the zeolite is selected from ZSM-5, ZSM-11, SAPO-11, and mixtures thereof, preferably ZSM-5.

In a further embodiment, the ZSM-5 has a silica to alumina ratio (Si/Al) in the range of 20 to 1500, more preferably 200 to 800.

Silicalite is a polymorph of silica having a structure analogous to the zeolites.

The catalyst system according to the present invention can shift product distribution of a hydrocarbon conversion process, particularly decreasing higher olefin and increasing lower olefin, even when a very small portion of the second layer is present. However, the larger portion of the second layer in the catalyst system does not always result in more reduction of the higher olefin due to equilibrium limitation.

In one embodiment, the weight ratio of the first layer to the second layer in the catalyst system is from 50:1 to 1:20, preferably 40:1 to 1:1.

The dehydrogenation active metal refers to a group of metals that are efficient for dehydrogenation of a hydrocarbon. Dehydrogenation is a reaction in which hydrogen is detached from a molecule. In one embodiment, the dehydrogenation active metal is selected from platinum, palladium, iridium, chromium, and mixtures thereof, preferably platinum.

In one embodiment, the solid support is selected from aluminium oxide, silicon dioxide, zirconium dioxide, titanium dioxide, magnesium oxide, calcium oxide, and mixtures thereof.

In another embodiment, the solid support comprises a mixed magnesium-aluminium oxide and/or a calcium-aluminium oxide.

Additional active metal, which acts to enhance catalytic activity of this first composition, such as potassium, tin, lanthanum, indium, yttrium, ytterbium, rhenium, and mixtures thereof, may be also present in the first composition, preferably tin, indium, and a mixture thereof.

In one embodiment, the first composition contains 0.01 to 25 wt % of the dehydrogenation active metal, preferably 0.05 to 20 wt % of the dehydrogenation active metal, more preferably 0.1 to 5 wt % of the dehydrogenation active metal, based on the total weight of the first composition.

In one embodiment, platinum is the dehydrogenation active metal, Al2O3 is the solid support and tin and/or potassium is the additional active metal in the first composition.

In another embodiment, platinum is the dehydrogenation active metal, SiO2 and ZrO2 are the solid support and yttrium and/or ytterbium is the additional active metal in the first composition.

In a further embodiment, platinum is the dehydrogenation active metal, a mixed magnesium-aluminium oxide and/or a mixed calcium-aluminium oxide is the solid support, and indium and/or tin is the additional active metal in the first composition.

In one embodiment, the mixed magnesium-aluminium oxide and the mixed calcium-aluminium oxide in the first composition are derived from a magnesium-aluminium or calcium-aluminium layered double hydroxide, which can be preferably obtained by subjecting a magnesium-aluminium or calcium-aluminium layered double hydroxide to a temperature in the range of 600-700° C., more preferably 600-650° C., for more than 2 hours, more preferably 3 to 10 hours.

Preferably, the first composition contains 0.005 to 2 wt % of the additional active metal based on the total weight of the first composition. Also preferably, is the additional active metal is supported on the solid support.

Preferably, the combined amount of the dehydrogenation active metal, the solid support, and the additional active metal present in the first composition is at least 90%, more preferably at least 95%, by weight of the first composition. In a particular embodiment, the first composition consists of the dehydrogenation active metal, the solid support, and optionally the additional active metal. In one embodiment, the transition metal of the second composition is selected from molybdenum, tungsten, rhenium, and mixtures thereof.

The transition metal is preferably tungsten, more preferably in the form of tungsten oxide.

In one embodiment, the inorganic support is selected from aluminium oxide, silicon dioxide, zirconium dioxide, titanium dioxide, zeolite, and mixtures thereof, preferably silicon dioxide or a mixture of silicon dioxide and zeolite.

In one embodiment, the second composition comprises tungsten on an inorganic support comprising a mixture of silicon dioxide and zeolite.

Preferably, the zeolite is selected from ZSM-5, X-zeolite, Y-zeolite, beta-zeolite, MCM-22, ferrierite, and mixtures thereof, more preferably Y-zeolite.

In another preferred embodiment, the second composition further comprises a mixed metal oxide, more preferably a mixed magnesium-aluminium oxide, a mixed calcium-aluminium oxide, or a mixture thereof, wherein the mixed metal oxide is preferably physically mixed with the transition metal on the inorganic support.

In a particularly preferred embodiment, the second composition contains tungsten oxide on an inorganic support comprising a mixture of silicon dioxide and Y-zeolite physically mixed with a mixed magnesium-aluminium oxide.

Even more preferably is the mixed magnesium-aluminium oxide derived from a magnesium-aluminium layered double hydroxide precursor.

In one embodiment, the second composition contains 1 to 15 wt % of the transition metal, even more preferably 5 to 10 wt % of the transition metal, based on the total weight of the second composition.

In one embodiment, the second composition further comprises a doping agent selected from zinc, gallium, indium, lanthanum, and mixtures thereof. Preferably, the doping agent is supported on the inorganic support.

Preferably, the doping agent is present in the second composition in an amount of 0.1-10 wt %, more preferably in an amount of 1-5 wt %, based on the total weight of the second composition.

Preferably, the combined amount of the transition metal, the inorganic support, the mixed metal oxide, and the optional doping agent present in the second composition is at least 90%, more preferably at least 95%, by weight of the second composition. In a particular embodiment, the second composition consists of the transition metal, the inorganic support, the mixed metal oxide, and optionally the doping agent. The first composition is preferably prepared by supporting all element precursors of the dehydrogenation active metal and the optional additional active metal on the solid support followed by a suitable heat treatment.

Similarly, the second composition is preferably prepared by supporting on the inorganic support all element precursors of the transition metal and the optional doping agent followed by a suitable heat treatment.

Element precursors are starting compounds containing the desired elements which can be converted to the desired form of the elements in the final hydrocarbon conversion catalyst by the suitable heat treatment. For example, the element precursors may include oxides, halides, alkoxides, nitrates, carbonates, formats, oxylates, amines, or hydroxides of the elements.

More preferably, the first composition is prepared by impregnating, preferably simultaneously (co-impregnation), the element precursors of the dehydrogenation active metal and the optional additional active metal, which are provided in solution form, on the solid support followed by calcination. The calcination is preferably carried out in oxidizing atmosphere, at a temperature in the range of 300-800° C. for 1-24 hours, even more preferably 400-600° C. for 2-10 hours.

Also more preferably, the second composition is prepared by impregnating, preferably sequentially, the element precursors of the transition metal and the optional doping agent, which are provided in solution form, on the inorganic support followed by calcination. The calcination is preferably carried out in oxidizing atmosphere, at a temperature in the range of 300-800° C. for 1-24 hours, even more preferably 400-600° C. for 2-10 hours.

The obtained first and second compositions from the preparation method described above are generally in the powder form with average size lower than 800 micrometers.

In one embodiment, the first composition and the second composition are physically mixed, preferably in a weight ratio of the first to the second composition from 1:10 to 10:1, more preferably 1:5 to 5:1, even more preferably 1:3 to 3:1, and even further preferably 1:2 to 2:1, to form the hydrocarbon conversion catalyst.

The hydrocarbon conversion catalyst can be in a powder form in one embodiment. In another embodiment, the hydrocarbon conversion catalyst can be also formed into a shape that is more suitable for industrial utilization, for example, pellet, tablet, extrudate, or sphere.

Physical mixing of the first and the second compositions can be carried out before or after shaping of the hydrocarbon conversion catalyst.

In one embodiment, the first composition and the second composition are separately formed into desired shapes, then the first composition formed into the desired shape and the second composition formed into the desired shape are physically mixed to obtain the hydrocarbon conversion catalyst.

In a more preferred embodiment, powder of the first composition and powder of the second composition are physically mixed to obtain the hydrocarbon conversion catalyst, and the obtained hydrocarbon conversion catalyst may then be formed into any desired shape.

In shaping of the first composition, the second composition, or the hydrocarbon conversion catalyst, a binding material can be added to facilitate formation of powder into the desired shape. Any binding material known in the an may be used.

In another embodiment, it is also possible that the first and the second compositions are provided in macroscopic scale layer form, wherein the first composition and the second composition are arranged as separate layers in a fixed-bed reactor, wherein a layer of the second composition is interposed between a layer of the first composition and the second layer comprising a cracking catalyst.

The cracking catalyst, which comprises a molecular sieve, is also formed into a layer structure. Someone skilled in the art will be easily aware how respective layers can be prepared and arranged in a reactor.

It is most preferred that the hydrocarbon feed stream passing through the reactor comes at first into contact with the hydrocarbon conversion catalyst and is subsequently contacted with the cracking catalyst.

In one embodiment, the first layer of the hydrocarbon conversion catalyst and the second layer comprising the cracking catalyst are arranged in the same reactor, more preferably a fixed-bed reactor.

It is favorable that when the first layer of the hydrocarbon conversion catalyst and the second layer comprising the cracking catalyst are arranged in the same reactor, they are separated by an inert material to prevent unintentional mixing of the two materials.

According to the invention is also a process for conversion of a hydrocarbon feed comprising a saturated hydrocarbon compound to olefin products comprising contacting a hydrocarbon feed stream with the catalyst system according to the invention.

In one embodiment, the hydrocarbon feed stream is passed through the catalyst system by contacting the hydrocarbon conversion catalyst first and the cracking catalyst second.

In another embodiment, the hydrocarbon feed stream comprises a paraffin selected from ethane, propane, butane, pentane, and mixtures thereof, preferably propane, butane, and a mixture thereof, even more preferably, the hydrocarbon feed stream is propane.

The process according to the present invention can be operated in a wide range of operating conditions. However, some specific ranges of operating conditions can result in high olefins production selectivity.

In one embodiment, the process for conversion of a hydrocarbon feed is carried out at a temperature in the range of 200-800° C., preferably 350-700° C., even more preferably 450-650° C.

In another embodiment, the process is carried out at a pressure in the range of 0.01 to 10 bar gauge, preferably 0.05 to 5 bar gauge.

The contact time needed to obtain a desirable yield of olefins products depends upon several factors, such as operating temperature, operating pressure, and catalyst activity. In one embodiment, the process is carried out at a weight hourly space velocity (WHSV) in the range of 0.01 to 20 $hr^{-1}$, preferably 0.05 to 5 $hr^{-1}$.

The process can be conducted in a batch manner or a continuous manner. For commercial scale, it is favorable that the process is continuously operated. Continuous operation can be performed with fixed bed, fluidized bed, or other techniques known in the art with fixed bed being typically preferred.

Prior to contacting with the hydrocarbon feed stream, the catalyst system may optionally be pretreated. The pretreatment condition may include contacting the catalyst system with an inert gas, an oxidizing gas, a reducing gas, or mixtures thereof, at an elevated temperature, preferably 250° C. to 850° C., more preferably 400° C. to 750° C., even more preferably 500° C. to 700° C. In one preferred embodiment, the pretreatment condition includes contacting the catalyst with a reducing gas, more preferably hydrogen, at a temperature in the range of 500-700° C. for approximately 0.5 to 8 hours.

After contact with the hydrocarbon feed stream at the operating condition, some poisonous substances, heavy hydrocarbons, and coke may deposit on the surface of the catalyst system. This normally affects activity of the catalyst mixture to gradually drop over time. A suitable regeneration can be performed on the used catalyst system to recover at least some of its activity.

In an embodiment, the hydrocarbon conversion process comprises a regeneration step wherein the regeneration step includes contacting the catalyst system with an oxidizing agent at a high temperature. The regeneration step should be carefully controlled to avoid overheating and destroying structure of the catalyst. In an embodiment, the regeneration step is carried out at a temperature in the range of 200° C. to 700° C., preferably 300° C. to 600° C. Other known regeneration techniques can be employed without limitation.

It was surprisingly found that a catalyst system of the present invention significantly reduces the amount of higher olefins in a hydrocarbon conversion process, but increases especially the amount of ethylene as a highly valued product.

A variety of catalyst systems according to the invention and one comparative example without a cracking catalyst have been prepared. It was surprisingly found by the inventors that catalyst systems according to the present invention show a significantly reduced selectivity of higher olefins, especially butenes, but increased selectivity of ethylene.

EXPERIMENTAL RESULTS

In the examples section below, the conversion of propane into olefins, preferably ethylene and butene, has been investigated using catalyst systems according to the present invention and one comparative example.

For each test, the reaction zone was set up so that the cracking catalyst is placed downstream to the hydrocarbon conversion catalyst. Weight ratio of the hydrocarbon conversion catalyst to the cracking catalyst used was approximately 40:1. C3H8 was fed to contact first with the hydrocarbon conversion catalyst and then with the cracking catalyst. The reaction zone was maintained at approximately 485 to 490° C., 0.1 bar gauge, and WHSV of approximately 0.15 to 0.2 $h^{-1}$. The results were measured at time on stream approximately 115-120 hours and are shown in the table below.

For the hydrocarbon conversion catalyst as used in the examples, a catalyst has been utilized with a first and a second composition.

The first composition containing 5 wt-% of platinum and 1.4 wt-% ytterbium on a $SiO_2$—$ZrO_2$ support was prepared by impregnating a solution of chloroplaiinic acid hexahydrate and a solution of ytterbium trinitrate onto powder of $SiO_2$—$ZrO_2$ mixture, then the resulting material was dried at 100° C. for 2 hours, followed by calcination under air at 700° C. for 3 hours.

For the second composition containing 7 wt % W, 4 wt % Y-zeolite, 9 wt % Mg—Al oxide, and balancing SiO2 was prepared by impregnating a solution of ammonium meta-tungstate hydrate on a mixture of SiO2 and Y-zeolite, then dried at 110° C. for 3 hours. Then the resulted material was then mixed with Mg—Al—CO3 layered double hydroxide followed by calcination under air at 550° C. for 2 hours.

1 part by weight of the first composition and 1 part by weight of the second composition were physically mixed together to form the hydrocarbon conversion catalyst.

Different cracking catalyst was used in each example as follow.

Example 1 (comparative): No cracking catalyst was used
Example 2 (comparative): a mixture of $SiO_2$ and $Al_2O_3$ was used
Example 3: a ZSM-5 zeolite with Si/Al ratio of 500 was used
Example 4: a silicalite was used
Example 5: a SAPO-34 zeolite was used
Example 6: a SAPO-11 zeolite was used
Example 7: a β-zeolite was used

TABLE 1

| | | Result | | | | | | | |
|---|---|---|---|---|---|---|---|---|---|
| | C3H8 | | Selectivity (% wt) | | | | | | |
| Example | Conversion (% wt) | Total Olefins | CH4 | C2H4 | C2H6 | C3H6 | C4H8 | C4H10 | C5+ |
| Example 1 | 21.842 | 61.034 | 0.721 | 1.462 | 21.991 | 41.241 | 16.496 | 14.361 | 2.979 |
| Example 2 | 22.353 | 65.496 | 0.867 | 3.302 | 20.870 | 41.910 | 19.052 | 11.570 | 1.230 |
| Example 3 | 21.812 | 55.365 | 0.946 | 4.125 | 23.048 | 35.939 | 13.996 | 12.507 | 2.307 |
| Example 4 | 21.574 | 47.887 | 1.074 | 3.939 | 24.368 | 30.365 | 11.611 | 17.197 | 4.051 |
| Example 5 | 23.127 | 57.680 | 0.891 | 2.835 | 23.072 | 37.907 | 15.330 | 13.479 | 2.601 |
| Example 6 | 23.028 | 56.044 | 0.978 | 3.283 | 23.354 | 37.236 | 13.916 | 12.453 | 2.559 |
| Example 7 | 21.401 | 60.015 | 0.964 | 3.292 | 22.557 | 38.708 | 16.903 | 12.329 | 2.049 |

It can be seen from the results above that when the catalyst system include zeolite or silicalite as a downstream layer, butenes selectivity was decreased while ethylene selectivity was increased comparing to when no cracking catalyst was used or a normal mixture of $SiO_2$—$Al_2O_3$ was used as a downstream layer of the catalyst system.

It can be further noticed that when ZSM-5 was used as a cracking catalyst, the increase of ethylene selectivity was highest. When β-zeolite was used, ethylene selectivity was increased but butenes selectivity was not reduced. When silicalite was used, butenes selectivity was decreased, and ethylene selectivity was increased, however, more of C5+ which is usually an undesired by-product was also produced.

The features disclosed in the foregoing description and in the claims may, both separately and in any combination thereof, be material for realizing the invention in diverse forms.

The features disclosed in the foregoing description and the claims may, both separately and in any combination thereof, be material for realizing the invention in diverse forms thereof.

The invention claimed is:

1. A catalyst system comprising:
   i. a first layer of a hydrocarbon conversion catalyst, the hydrocarbon conversion catalyst comprising:
      a first composition comprising a dehydrogenation active metal on a solid support, the solid support comprising aluminum oxide, silicon dioxide, zirconium dioxide, titanium dioxide, magnesium oxide, calcium oxide, or a mixture thereof; and
      a second composition comprising a transition metal on an inorganic support, the inorganic support comprising silicon dioxide, a zeolite, or a mixture thereof; and
   ii. a second layer comprising a cracking catalyst, the cracking catalyst comprising a molecular sieve,
   wherein a weight ratio of the first layer to the second layer is from 50:1 to 1:20.

2. The catalyst system according to claim 1, wherein the molecular sieve is a zeolite and/or silicalite.

3. The catalyst system according to claim 2, wherein the molecular sieve of the cracking catalyst is a zeolite selected from the group consisting of ZSM-5, ZSM-11, SAPO-11, and mixtures thereof.

4. The catalyst system according to claim 1, wherein the dehydrogenation active metal is selected from the group consisting of platinum, palladium, iridium, chromium, and mixtures thereof.

5. The catalyst system according to claim 1, wherein the solid support comprises aluminum oxide, a mixture of silicon dioxide and zirconium dioxide, a mixture of magnesium oxide and aluminum oxide, or a mixture of calcium oxide and aluminum oxide.

6. The catalyst system according to claim 1, wherein the transition metal is selected from the group consisting of molybdenum, tungsten, rhenium, and mixtures thereof.

7. The catalyst system according to claim 1, wherein the second composition further comprises a mixed magnesium-aluminium oxide or a mixed calcium-aluminium oxide.

8. The catalyst system of claim 1, wherein the zeolite of the inorganic support is selected from the group consisting of ZSM-5, X-zeolite, Y-zeolite, beta-zeolite, MCM-22, ferrierite, and mixtures thereof.

9. The catalyst system of claim 1, wherein the transition metal is present in the second composition in an amount from 1 to 15 percent by weight.

10. The catalyst system of claim 1, wherein the second composition further comprises a doping agent selected from the group consisting of zinc, gallium, indium, lanthanum, and mixtures thereof.

11. The catalyst system of claim 10, wherein the doping agent is present in the second composition in an amount from 0.1 to 10 percent by weight.

12. The catalyst system of claim 1, wherein the first composition and the second composition are present as a physical mixture.

13. The catalyst system of claim 1, wherein the weight ratio of the first layer to the second layer is from 40:1 to 1:1.

14. A process for conversion of a hydrocarbon feed stream comprising a paraffin to a product stream comprising olefins, the process comprising contacting the hydrocarbon feed stream with the catalyst system according to claim 1.

15. The process according to claim 14, wherein the paraffin is selected from the group consisting of ethane, propane, butane, pentane, and mixtures thereof.

16. The process according to claim 14, wherein the process is carried out at a temperature in the range of 200–800° C.

17. The process according to claim 14, wherein the hydrocarbon feed stream contacts the hydrocarbon conversion catalyst first and the cracking catalyst second.

18. The process according to claim 14, wherein the catalyst system is pretreated by contacting the catalyst system with an inert gas, an oxidizing gas, a reducing gas, or mixtures thereof, at a temperature in the range of 250° C. to 850° C., prior to contacting with the hydrocarbon feed stream.

19. The process of claim 14, wherein the hydrocarbon feed stream comprises propane, the product stream comprises ethylene, and a selectivity to ethylene in product stream is increased, relative to a process in which the cracking catalyst of the catalyst system is absent.

* * * * *